United States Patent [19]

Felix

[11] 4,238,405
[45] Dec. 9, 1980

[54] FUNGICIDAL 1,2-DICHLOROCYANOVINYL COMPOUNDS

[75] Inventor: Raymond A. Felix, El Cerrito, Calif.

[73] Assignee: Stauffer Chemical Company, Westport, Conn.

[21] Appl. No.: 834,215

[22] Filed: Sep. 19, 1977

[51] Int. Cl.$^3$ ............ A01N 37/34; A01N 41/10; C07C 121/30; C07C 121/48

[52] U.S. Cl. ............ 260/464; 260/239 BF; 260/465 G; 260/465.4; 260/465.7; 260/940; 544/316; 544/319; 548/166; 548/173; 548/316; 548/319; 548/329; 548/337; 424/210; 424/251; 424/244; 424/270; 424/273 R; 424/273 B

[58] Field of Search ............ 260/465.7, 464

[56] References Cited

U.S. PATENT DOCUMENTS

| | | | |
|---|---|---|---|
| 3,000,927 | 9/1961 | Birum et al. | 260/465 |
| 3,044,927 | 7/1962 | Heininger et al. | 260/465 |
| 3,078,298 | 2/1963 | Gregory et al. | 260/465.7 |
| 3,140,306 | 7/1964 | Heininger | 260/465.7 |
| 3,159,532 | 12/1964 | Heininger et al. | 260/465 |
| 3,541,119 | 11/1970 | Richter et al. | 260/397.6 |
| 4,021,482 | 5/1977 | Schempp | 260/561 S |
| 4,079,148 | 3/1978 | Oeckl et al. | 260/465.7 |

FOREIGN PATENT DOCUMENTS 2500265  7/1976  Fed. Rep. of Germany ........ 260/465.7

OTHER PUBLICATIONS

Horsfall, Fungicides and Their Action, (Mass., 1945), pp. 151-152.

Primary Examiner—Alton D. Rollins
Attorney, Agent, or Firm—Michael J. Bradley

[57] ABSTRACT

Novel biocidal compounds have the general structural formula

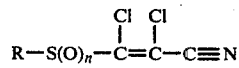

wherein n is 0, 1, or 2 and R is alkyl, alkylcarbalkoxy, cyclohexyl, halophenyl, benzyl, N,N-di-lower alkyl carbamoyl, hexamethyleneimino carbonyl, pyrimidyl, lower alkyl substituted pyrimidyl, benzimidazole, lower alkyl substituted imidazole, benzothiazole and O,O-di-lower alkyl thiophosphoryl; with the proviso that when n is 0, R is other than alkyl or cyclohexyl.

17 Claims, No Drawings

FUNGICIDAL 1,2-DICHLOROCYANOVINYL COMPOUNDS

DETAILED DESCRIPTION OF THE INVENTION

This invention relates to novel biocidal 1,2-dichlorocyanovinyl sulfides, sulfoxides and sulfones.

The novel compounds of this invention have the general structural formula

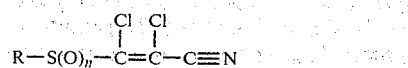

wherein n is 0, 1, or 2 and R is selected from the group consisting of alkyl, alkylcarbalkoxy, cyclohexyl, halophenyl, benzyl, N,N-di-lower alkyl carbamoyl, hexamethyleneimino carbonyl, pyrimidyl, lower alkyl substituted pyrimidyl, benzimidazole, lower alkyl substituted imidazole, benzothiazole and O,O-di-lower alkyl thiophosphoryl; with the proviso that when n is O, R is other than alkyl or cyclohexyl.

In the above description of the compounds of this invention, where R is alkyl the term refers to straight and branched chain alkyl radicals containing 1 to 12 carbon atoms. Illustrative examples include methyl, ethyl, propyl, butyl, sec-butyl, tert-butyl, pentyl, neopentyl, hexyl, heptyl, nonyl, decyl, dodecyl and the like and their position isomers. Particularly preferred are straight or branched chain alkyl radicals containing 3 to 9 carbon atoms. Alkylcarbalkoxy refers to radicals of the formula

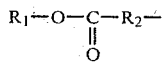

where $R_1$ is a lower alkyl radical containing 1 to 4 carbon atoms and $R_2$ is a divalent alkylene radical containing 1 to 4 carbon atoms. Illustrative examples include methylcarbethoxy, ethylcarbomethoxy, methylcarbopropoxy, propylcarbethoxy, and the like.

Where lower alkyl substituents are specified, the term includes straight and branched chain alkyl radicals containing 1 to 4 carbon atoms, i.e., methyl, ethyl, propyl, isopropyl, butyl, isobutyl, sec-butyl and tert-butyl.

The compounds are prepared by reacting trichloroacrylyl chloride with aqueous ammonia at a temperature of about −30° C. to about 100° C., preferably about 0° C. to about 20° C., to form trichloroacrylylamide. The trichloroacrylylamide is then dehydrated using a dehydrating agent such as, for example, phosphoryl chloride, phosphorus pentoxide, trifluoroacetic anhydride, pyridine or thionyl chloride. The resulting trichloroacrylonitrile is reacted with the appropriate mercaptan in the presence of an acid acceptor, such as, for example, triethylamine, potassium t-butoxide, sodium methoxide, or a phase transfer catalyst with sodium hydroxide, for example, benzyl triethylammonium chloride and sodium hydroxide, to form the desired sulfide. The sulfoxide and sulfone derivatives are formed by reacting the sulfide with an oxidizing agent such as hydrogen peroxide or organic peracids, such as peracetic acid, performic acid, or m-chloroperoxybenzoic acid. The resulting product is a cis-trans-isomer mixture of the 1,2-dichlorocyanovinyl compound. Separation of the isomers can be effected by standard procedures, if desired, but is not necessary for utilization of these compounds as biocides.

This preparation can be illustrated by the following equations:

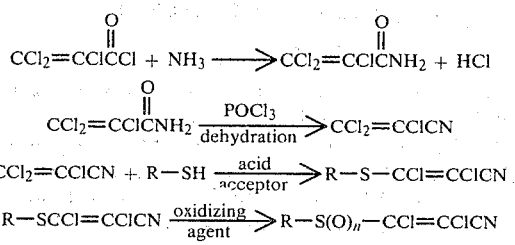

where n is 1 or 2.

The novel compounds of this invention are biocides in that they prevent, control or inhibit the growth of microorganisms selected from bacteria and fungi. Thus, another embodiment of this invention comprises a method of controlling microorganisms selected from bacteria and fungi by applying to the locus where such control is desired an effective amount of the novel compounds described above. Some of the compounds of this invention are particularly useful as soil fungicides, controlling the growth of fungi when incorporated into soil. The effective amount of the particular compound used will vary depending on the degree of control desired. Generally, about 0.5 to about 6 pounds per acre, preferably about 1 to about 4 pounds per acre, will be employed. When used as a foliar fungicide to protect vegetation from fungus growth about 0.5 to about 6, preferably about 1 to about 4, pounds of compound dissolved or dispersed in 100 gallons of water should be sprayed on the foilage to be protected. For other uses of the compounds of this invention to control microorganisms, one skilled in the art will be able, without undue experimentation, to determine the effective amount of the compound required to provide the desired degree of control.

Compounds of the above formula where n is 0 and R is alkyl or cyclohexyl exhibit little, if any, biocidal activity when tested at the screening rates. See Table II below. These compounds, however, are novel and are useful in preparing biocidally active sulfoxides and sulfones. The compounds have the general structural formula:

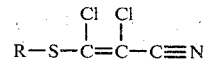

wherein R is alkyl or cyclohexyl.

The following examples illustrate the preparation of typical compounds of this invention and demonstrate their utility as biocides.

EXAMPLE 1

This example illustrates the preparation of isopropyl 1,2-dichloro-2-cyanovinyl sulfide.

In a reaction vessel, 6.3 grams trichloroacrylylnitrile, 3.1 grams isopropyl mercaptan and 300 milligrams benzyl triethylammonium chloride were dissolved in 5 milliliters of benzene. To this was added 3.4 grams of 50% sodium hydroxide dissolved in 3 milliliters of water. The reaction mixture was stirred for four hours while maintaining the temperature at about 25° C. Then 100 milliliters water was added and the reaction mixture was extracted with methylene dichloride. The combined organic layers were dried over anhydrous magnesium sulfate and stripped of volatiles. A yield of 8.0 grams of a light yellow oil having a refractive index—$n_D^{30}=1.5080$ was obtained. The structure of the product was confirmed by IR and NMR.

EXAMPLE 2

This example illustrates the preparation of isopropyl 1,2-dichloro-2-cyanovinyl sulfoxide.

Four grams of isopropyl 1,2-dichloro-2-cyanovinyl sulfide, prepared in Example 1, was dissolved in 50 milliliters methylene dichloride and the solution was cooled to 0° C. Four grams of solid 85% m-chloroperbenzoic acid was added in portions over one half hour. The reaction mixture was stirred for two hours while the temperature was maintained at 0° C. The reaction mixture was then filtered and washed with 5% potassium carbonate solution. The organic layer was dried over anhydrous magnesium sulfate and stripped of volatiles. A yield of 3 grams of isopropyl 1,2-dichloro-2-cyanovinyl sulfoxide having a refractive index—$n_D^{30}=1.5112$ was obtained. The structure of the product was confirmed by IR and NMR.

EXAMPLE 3

This example illustrates the preparation of isopropyl 1,2-dichloro-2-cyanovinyl sulfone.

Three grams of isopropyl, 1,2-dichloro-2-cyanovinyl sulfoxide, prepared in Example 2, was dissolved in 25 milliliters methylene dichloride and the resulting solution was cooled to 0° C. Then 3.3 grams of 85% m-chloroperbenzoic acid was added. The reaction mixture was permitted to stir at 25° C. overnight. The reaction mixture was then filtered and washed with 5% potassium carbonate solution. The organic layer was dried over anhydrous magnesium sulfate and stripped of volatiles. A yield of 3.0 grams of a liquid product having a refractive index—$n_D^{30}=1.5020$ was obtained. The structure of the product was confirmed by IR and NMR.

EXAMPLE 4

This example illustrates the preparation of 1,2-dichloro-2-cyanovinyl-2',4',5'-trichlorophenyl sulfide.

In a reaction vessel, 6.4 grams of 2,4,5-trichlorothiophenol and 4.7 grams of trichloroacrylylnitrile were dissolved in 25 milliliters of methylene dichloride. Then 3.0 grams triethylamine was added and the reaction mixture was permitted to stir overnight at room temperature. The reaction mixture was diluted with 100 milliliters of water and extracted with methylene dichloride. The combined organic layers were dried over anhydrous magnesium sulfate and stripped of volatiles. A yield of 8.6 grams of a yellow solid having a melting point—m.p.=89°-105° C. was obtained. The structure of the product was confirmed by NMR and IR.

EXAMPLE 5

This example illustrates the preparation of 1,2-dichloro-2-cyanovinyl-2-benzothiazole sulfide.

A solution of 3.3 grams 2-mercaptobenzothiazole and 3.1 grams trichloroacrylylnitrile dissolved in 25 milliliters methylene chloride was prepared. While the reaction mixture was vigorously stirred, 2.2 grams triethylamine was added. The reaction mixture was stirred overnight at 25° C. The reaction mixture was diluted with 100 milliliters of water and extracted with methylene dichloride. The combined organic layers were dried over anhydrous magnesium sulfate and stripped of volatiles. A yield of 4.8 grams of an orange solid having a melting point—m.p.=80°-86° C. was obtained. The structure of the product was confirmed by IR and NMR.

EXAMPLE 6

This example illustrates the preparation of O,O-diethyl-S-(1,2-dichloro-2-cyanovinyl) phosphorodithioate.

A solution of 4.4 grams of O,O-diethyl dithiophosphoric acid potassium salt and 3.1 grams of trichloroacrylylnitrile dissolved in 25 milliliters acetone was prepared. This reaction mixture was stirred overnight at 25° C. Then 100 milliliters of ether was added and the solution was washed with water. The organic layer was dried over anhydrous magnesium sulfate and stripped of volatiles. A yield of 6.6 grams of an amber oil having a refractive index—$n_D^{30}=1.5079$ was obtained. The structure of the product was confirmed by IR and NMR.

Other compounds illustrative of those embodied in this invention have been prepared. These compounds, including those whose preparation is described in detail above, are listed in the following Table I. The compounds have been assigned numbers which are then used throughout the remainder of the specification.

TABLE I $$R-S(O)_n-\underset{Cl}{\underset{|}{C}}=\underset{Cl}{\underset{|}{C}}-C\equiv N$$

| Compound No. | n | R |
|---|---|---|
|  | 0 | $-C_2H_5$ |
| 2 | 1 | $-C_2H_5$ |
| 3 | 0 | $-CH_2$<$\begin{array}{c}CH_3\\CH_3\end{array}$ |
| 4 | 1 | $-CH_2$<$\begin{array}{c}CH_3\\CH_3\end{array}$ |
| 5 | 2 | $-CH_2$<$\begin{array}{c}CH_3\\CH_3\end{array}$ |
| 6 | 0 | -n-$C_4H_9$ |
| 7 | 1 | -n-$C_4H_9$ |
| 8 | 0 | -sec.-$C_4H_9$ |
| 9 | 1 | -sec.-$C_4H_9$ |
| 10 | 2 | -sec.-$C_4H_9$ |
| 11 | 0 | -tert-$C_4H_9$ |
| 12 | 0 | $-CH_2-CH_2-\underset{\underset{CH_3}{|}}{CH}-CH_3$ |
| 13 | 1 | $-CH_2-CH_2-\underset{\underset{CH_3}{|}}{CH}-CH_3$ |
| 14 | 2 | $-CH_2-CH_2-\underset{\underset{CH_3}{|}}{CH}-CH_3$ |
| 15 | 0 | -n-$C_8H_{17}$ |
| 16 | 1 | -n-$C_8H_{17}$ |
| 17 | 2 | -n-$C_8H_{17}$ |
| 18 | 0 | -n-$C_9H_{19}$ |
| 19 | 1 | -n-$C_9H_{19}$ |
| 20 | 2 | -n-$C_9H_{19}$ |
| 21 | 0 | $-CH_2-O-\overset{\overset{O}{\|}}{C}-C_2H_5$ |
| 22 | 1 | $-CH_2-O-\overset{\overset{O}{\|}}{C}-C_2H_5$ |

TABLE I-continued $$R-S(O)_n-\underset{Cl}{C}=\underset{Cl}{C}-C\equiv N$$

| Compound No. | n | R |
|---|---|---|
| 23 | 0 | 2-thienyl |
| 24 | 1 | 2-thienyl |
| 25 | 2 | 2-thienyl |
| 26 | 0 | 4-chlorophenyl |
| 27 | 0 | 3,4-dichlorophenyl |
| 28 | 1 | 3,4-dichlorophenyl |
| 29 | 2 | 3,4-dichlorophenyl |
| 30 | 0 | —CH$_2$—phenyl |
| 31 | 0 | —C(O)—N(CH$_2$CH$_2$CH$_3$)$_2$ |
| 32 | 0 | —C(O)—N(piperidinyl) [—C(O)—N(CH$_2$CH$_2$CH$_2$CH$_2$CH$_2$)] |
| 33 | 0 | pyrimidin-2-yl |
| 34 | 0 | 4-methylpyrimidin-2-yl |
| 35 | 0 | benzimidazol-2-yl |
| 36 | 0 | 1-methylimidazol-2-yl (—C=N—CH=CH—N(CH$_3$)—) |
| 37 | 0 | benzothiazol-2-yl |
| 38 | 1 | benzothiazol-2-yl |
| 39 | 0 | —P(=S)(OC$_2$H$_5$)$_2$ |

As stated above, the novel compounds of this invention are biocides. The compounds were tested for bactericidal and fungicidal activity using the following test procedures.

IN VITRO BIOCIDE TESTS

In-Vitro Bactericide Bioassay

Test chemicals are diluted in acetone to a concentration of 2500 ppm. Test cultures are prepared by adding 0.1 milliliters of cultures of *E. Coli, Staph. aureus*, or *Erwinia amylovora* to 16×100 millimeter test tubes containing 5 milliliters of sterile nutrient broth. One-tenth milliliter of the stock chemical solution is then added to each test tube for a final concentration of 50 ppm, and the tubes are maintained at 27° C. for one week. Each tube is then examined for the presence or absence of turbidity due to the growth of the bacterium. Chemicals which show control at 50 ppm are retested at progressively lower levels until the minimum concentration giving 75% or greater control is determined. The results are shown in Table II.

In-Vitro Fungicide Bioassay

Test chemicals are diluted in acetone to a concentration of 2500 ppm. Test cultures are prepared by adding 0.1 milliliters of cultures of either *Aspergillus niger* or *Penicillium italicum* to 16×100 millimeter test tubes containing 5 milliliters of sterile malt extract broth. One-tenth milliliter of the stock chemical solution is then added to each test tube for a final concentration of 50 ppm, and the tubes are maintained at 27° C. for one week. Each tube is then examined for the presence or absence of a mycelial mat. Chemicals which show control at 50 ppm are retested at progressively lower levels until the minimum concentration giving 75% or greater control is determined. The results are shown in Table II.

FOLIAR PREVENTATIVE FUNGICIDE TESTS

1. Bean Rust

Test chemicals are dissolved in an appropriate solvent and then further diluted with a 50:50 acetone:water solution. Pinto bean plants (*Phaseolus vulgaris*), approximately 15 centimeters tall, are inverted and dipped into the solution for 2–3 seconds. Test concentrations range from 1000 ppm downward. After the leaves have dried, they are inoculated with a water suspension of spores of the bean rust fungus (*Uromyces phaseoli*) and the plants are placed in an environment of 100% humidity for 24 hours. The plants are then removed from the humidity chamber and held until disease pustules appear on the leaves. Effectiveness is recorded as percent reduction in number of pustules as compared to untreated inoculated plants. The results are shown in Table II.

2. Bean Powdery Mildew

Test chemicals are dissolved in an appropriate solvent and then further diluted with a 50:50 acetone:water solution. Pinto bean plants (*Phaseolus vulgaris*), approximately 15 centimeters tall, are inverted and dipped into the solution for 2–3 seconds. Test concentrations range from 1000 ppm downward. After the leaves have dried, they are dusted with spores of the powdery mildew fungus (*Erysiphe polygoni*) and the plants are retained in the greenhouse until the fungal growth appears in the leaf surface. Effectiveness is recorded as percent of the leaf surface free of fungal growth as compared to untreated inoculated plants. The results are shown in Table II.

SOIL FUNGICIDE TEST

*Rhizoctonia solani*

*Rhizoctonia solani* is cultured on Potato Dextrose Agar plates. After several weeks, sclerotia are formed. To prepare the inoculum, portions of the plates with the heaviest sclerotial formulation are placed in a blender with about 60–75 milliliters of water. After a short blending period, a thick slurry of sclerotia, mycelia, water and agar is formed.

Five milliliters of the above suspension are added to 4 Kg of sterile soil in a 5 gallon soil incorporator and thoroughly mixed into the soil. Four hundred grams of the inoculated soil is weighed into each one pint paper can (Fonda #106) and a small quantity of clean dry sand is placed in a depression in the center of the soil. One milliliter of solvent (Acetone/$H_2O$) containing an appropriate amount of the test compound is then added to the sand in each pot and the chemicals are thoroughly incorporated into the soil. Final concentrations of the test chemicals are 50, 25, 10, 5, 1 ppm. Finally, 5 pinto bean (*Phaseolus sp.*) seeds are planted in each pot.

The pots are maintained in a greenhouse at 21° C. for 3 weeks. Efficacy of the test chemicals is determined by examining the stems of the plants for lesions. The results are shown in Table III.

*Fusarium solani*

*Fusarium solani* f. sp. *phseoli* is cultured via mass transfer on V-8 agar plates. The spores are washed off the plates with tap water. Spore concentration is checked with a hemocytometer and is adjusted to give a final concentration of macroconidia of $2 \times 10^6$ conidia/milliliter.

Four Kg sterile soil is placed in a 19L (5 gallon) soil incorporator. Four milliliters of the conidial suspension is added to the soil which is mixed to give a final concentration of $2 \times 10^3$ conidia/gram soil. Four hundred grams of the inoculated soil is weighed into each one pint paper can (Fonda #106) and a small quantity of clean dry sand is placed in a depression in the center of the soil. One milliliter of solvent (acetone/$H_2O$) containing an appropriate amount of the test compound is then added to the sand in each pot and the chemicals are thoroughly incorporated into the soil. Final concentrations of the test chemicals are 50, 25, 10, 5, 1 ppm. Finally, 5 pinto beans (Phaseolus sp.) seeds are planted in each pot.

The pots are maintained in a greenhouse at 21° C. for three weeks. Efficacy of the test chemicals is determined by examining the stems of the plants for lesions. The results are shown in Table III.

TABLE II

| | IN VITRO | | | | | FOLIAR | |
|---|---|---|---|---|---|---|---|
| Compound No. | Aspergillus niger | Penicillium italicum | E. Coli | Staph. aureus | Erwinia amylovora | Bean Rust | Bean Mildew |
| 1 | 50 | (25) | >50 | 50 | >50 | >1000 | >1000 |
| 2 | 5 | 0.5 | 25 | 10 | 0.5 | >1000 | >1000 |
| 3 | >50 | >50 | >50 | >50 | >50 | >1000 | >1000 |
| 4 | 5 | 5 | 25 | 5 | (1) | >1000 | >1000 |
| 5 | 5 | 5 | >50 | 25 | 5 | 100 | >1000 |
| 6 | >50 | >50 | >50 | 25 | >50 | >1000 | >1000 |
| 7 | 5 | (0.5) | >50 | 5 | 10 | >1000 | >1000 |
| 8 | >50 | >50 | >50 | >50 | >50 | >1000 | 1000 |
| 9 | (5) | 5 | 25 | 5 | 5 | >1000 | >1000 |
| 10 | 5 | (1) | >50 | 10 | 5 | >1000 | >1000 |
| 11 | >50 | >50 | >50 | >50 | >50 | >1000 | >1000 |
| 12 | >50 | >50 | >50 | 25 | >50 | >1000 | >1000 |
| 13 | 5 | 0.5 | >50 | 10 | 10 | >1000 | >1000 |
| 14 | 1 | 1 | >50 | 10 | 25 | >1000 | >1000 |
| 15 | >50 | >50 | >50 | >50 | >50 | >1000 | >1000 |
| 16 | 0.5 | 0.125 | >50 | 1.0 | 5 | >1000 | 1000 |
| 17 | (1) | (0.5) | >50 | 10 | 25 | >1000 | 500 |
| 18 | >50 | >50 | >50 | >50 | >50 | >1000 | >1000 |
| 19 | 5 | (0.25) | >50 | (5) | 25 | 500 | >1000 |
| 20 | (5) | 5 | >50 | 25 | >50 | 500 | >1000 |
| 21 | (5) | 25 | >50 | 25 | (50) | >1000 | >1000 |
| 22 | 5 | 5 | >50 | 5 | 25 | >1000 | >1000 |
| 23 | >50 | >50 | >50 | >50 | >50 | >1000 | >1000 |
| 24 | 5 | 1 | >50 | 1 | 5 | >1000 | >1000 |
| 25 | (1) | (.25) | >50 | 25 | 25 | >1000 | >1000 |
| 26 | 5 | 1 | >50 | 5 | >50 | >1000 | >1000 |
| 27 | 1 | 5 | >50 | 0.016 | >50 | >1000 | >1000 |
| 28 | 0.5 | 0.5 | >50 | 0.063 | 10 | >1000 | >1000 |
| 29 | 5 | 0.5 | >50 | 0.5 | 25 | >1000 | >1000 |

TABLE II-continued

| Compound No. | IN VITRO | | | | | FOLIAR | |
|---|---|---|---|---|---|---|---|
| | Aspergillus niger | Penicillium italicum | E. Coli | Staph. aureus | Erwinia amylovora | Bean Rust | Bean Mildew |
| 30 | 5 | 5 | >50 | 5 | >50 | >1000 | >1000 |
| 31 | 10 | 10 | >50 | 5 | >50 | >1000 | >1000 |
| 32 | 10 | 5 | >50 | 1 | 50 | >1000 | >1000 |
| 33 | 5 | 5 | >50 | 5 | 25 | >1000 | >1000 |
| 34 | 10 | 5 | >50 | 5 | 50 | >1000 | >1000 |
| 35 | 10 | 1 | >50 | 0.5 | (10) | 500 | >1000 |
| 36 | (25) | (5) | >50 | 10 | 25 | >1000 | >1000 |
| 37 | 0.5 | 0.125 | >50 | 0.25 | 5 | 1000 | >1000 |
| 38 | 5 | 0.25 | >50 | 0.25 | 1 | 1000 | >1000 |
| 39 | 25 | 25 | >50 | 5 | 10 | >1000 | >1000 |

In the above Table II:
\>indicates that the compound did not control the growth of that species of bacteria or fungi at the given concentration of the test compound
()indicates that partial control of that species of bacteria or fungi was achieved at the given concentration of the test compound

TABLE III

| | SOIL FUNGICIDE TEST | |
|---|---|---|
| Compound No. | Rhizoctonia solani, ppm | Fusarium solani, ppm |
| 4* | 1.4 | .8 |
| 4 | 1.8 | 1.5 |
| 5 | 1.6 | 1.2 |
| 7 | 6 | 2.3 |
| 10 | 23 | 1.8 |
| 13 | 7 | — |
| 16 | 50 | 11.5 |
| 17 | 50 | 16.5 |
| 19 | 23 | 25 |
| 20 | 35 | 10 |
| 22 | 7 | 7.5 |
| 24 | — | 2.4 |
| 28 | 28 | 25 |
| 35 | 32 | 50 |

*Compound No. 4 was run through the soil fungicide evaluation twice, all other compounds were tested once.

The novel compounds of this invention are generally applied to the locus where control of bacteria or fungi is desired in the form of formulations containing an effective amount of the compound and an inert carrier. Such formulations generally take the form of dusts, wettable powders, solutions, emulsifiable concentrates or the like. Such formulations normally contain up to about 80% by weight of the active ingredient.

Dusts are free-flowing powder compositions containing the active compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired.

Wettable powders are finely divided compositions comprising a particulate carrier impregnated with the active compound and additionally containing one or more surface active agents. The surface active agents promote rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in *Pesticide Formulations* by Wade Van Valkenburg, Marcel Dekker, Inc., N.Y., 1973 at pages 79–84.

Granules comprise the active compound impregnated on a particulate inert carrier having a particle size of 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The active compounds can also be applied in the form of a solution in a suitable solvent. Solvents frequently used in biocidal formulations include kerosene, fuel oil, xylene, petroleum fractions with boiling ranges above xylene, and aromatic petroleum fractions rich in methylated naphthalenes.

Emulsifiable concentrates consist of an oil solution of the active compound along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

What is claimed is:

1. A compound having the general structural formula

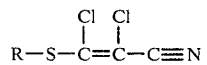

wherein R is alkyl or cyclohexyl.

2. The compound of claim 1 wherein R is ethyl.
3. The compound of claim 1 wherein R is isopropyl.
4. The compound of claim 1 wherein R is n-butyl.
5. The compound of claim 1 wherein R is sec-butyl.
6. The compound of claim 1 wherein R is tert-butyl.
7. The compound of claim 1 wherein R is 1-methylbutyl.
8. The compound of claim 1 wherein R is n-octyl.
9. The compound of claim 1 wherein R is n-nonyl.
10. The compound of claim 1 wherein R is cyclohexyl.
11. The compound having the structural formula

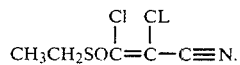

12. The compound having the structural formula

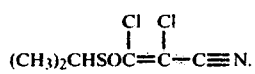
13. The compound having the structural formula
14. The compound having the structural formula
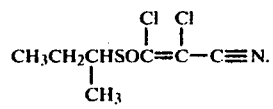
15. The compound having the structural formula
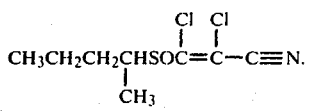
16. The compound having the structural formula
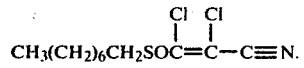
17. The compound having the structural formula
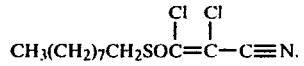
* * * * *